(12) United States Patent  
Fietz

(10) Patent No.: US 8,528,387 B2  
(45) Date of Patent: Sep. 10, 2013

(54) TESTING OF CONCRETE USING EXISTING VOIDS WITHIN CONCRETE

(76) Inventor: Dale Howard Fietz, Petaluma, CA (US)

(*) Notice: Subject to any disclaimer, the term of this patent is extended or adjusted under 35 U.S.C. 154(b) by 89 days.

(21) Appl. No.: 13/186,053

(22) Filed: Jul. 19, 2011

(65) Prior Publication Data

US 2013/0019665 A1    Jan. 24, 2013

(51) Int. Cl.
*G01N 3/42* (2006.01)

(52) U.S. Cl.
USPC .................................... 73/81; 73/78

(58) Field of Classification Search
USPC ............................................. 73/78
See application file for complete search history.

(56) References Cited

U.S. PATENT DOCUMENTS

| | | | |
|---|---|---|---|
| 3,029,631 A * | 4/1962 | Borgersen et al. | 73/81 |
| 3,283,566 A | 11/1966 | Fietz | |
| 3,640,126 A | 2/1972 | Te'eni | |
| 4,692,300 A * | 9/1987 | Grespin | 376/245 |
| 4,748,855 A | 6/1988 | Barnoff | |
| 5,773,722 A | 6/1998 | Helderman | |

* cited by examiner

Primary Examiner — Hezron E Williams
Assistant Examiner — Paul West
(74) Attorney, Agent, or Firm — Steven A. Nielsen; Allman & Nielsen P.C. NielsenPatents.com

(57) ABSTRACT

A penetration head and related apparatuses are placed within a void to measure the in-place compressive strength of the surrounding material. An electronic load cell is attached to the penetration head and is forced against an opposite side of the void. A hydraulic ram or other device is connected between the penetration head and load cell. As the hydraulic ram pushes the penetration head and load cell in opposite directions and into the interior walls of the void, penetration depth is measured and mapped to load and material hardness is derived.

9 Claims, 5 Drawing Sheets

TESTING OF CONCRETE USING EXISTING VOIDS WITHIN CONCRETE

COPYRIGHT AND TRADEMARK NOTICE

This application includes material which is subject or may be subject to copyright and/or trademark protection. The copyright and trademark owner(s) has no objection to the facsimile reproduction by any of the patent disclosure, as it appears in the Patent and Trademark Office files or records, but otherwise reserves all copyright and trademark rights whatsoever.

BACKGROUND OF THE INVENTION (1) Field of the Invention

The invention generally relates to means and methods of testing the strength of rigid materials such as concrete. More particularly, the invention relates to the placement of testing equipment within voids of the tested material.

(2) Description of the Related Art

Testing of concrete is known in the related art, as concrete and similar materials have been and continue to be widely used. An excellent prior art example is U.S. Pat. No. 3,283,566 issued on Nov. 8, 1966 to the inventor of the present invention, Dale Howard Fietz. The '566 patent entitled "Material Hardness Tester" discloses a strain gauge placed within a void and an assembly of mechanical components driving by an external torque wrench. Friction and other variables needed to be calculated in order to determine material hardness.

U.S. Pat. No. 3,640,126 issued on Feb. 8, 1972 to Moshe Te'eni discloses a system of using a void with a large base and narrow neck. An apparatus is placed in the void, expanded to fill the large base section and then withdrawn until concrete is dislodged. The Te'eni method required the drilling of a non-uniform cylinder and the use of complex mechanical components subject to many frictional forces. Te'eni would occasionally result in material being pulled out during testing, destroying the surrounding material and preventing any possibility of repeating a test in the same location.

U.S. Pat. No. 4,748,855 issued on Jun. 7, 1998 to Barnoff presents a complex system comprising a force rod and bearing shoes fitted into a cylindrical housing. The housing is lowered into a void or cylinder of concrete. The force rod comprises various cam structures subject to frictional forces and material hardness is derived by the measurement of torque to the force rod. Frictional forces from the cam section of the force rod and bearing shoe linkage needed to be calculated and such frictional forces directly compromised the integrity of the test results. Thus, there is a need in the art for improved means and methods of using existing cylinders, core holes or voids to measure material properties.

BRIEF SUMMARY OF THE INVENTION

The present invention overcomes shortfalls in the related art by presenting an unobvious and unique combination, configuration of mechanical and electrical components used to measure material properties. The present invention teaches away from the prior art by not destroying tested material and not requiring the use or drilling of non-uniform voids or core holes.

Further advantages of the present invention include, but are not limited to:

Standard uniform cylinder voids, typically found after concrete corings are made, may be used without additional cost or damage to the tested material.

Embodiments of the disclosed device may be economically adapted to various core diameters and various core depths. Multiple test locations within a single void may be quickly tested by varying the depth and radial position of the disclosed penetration head.

Immediate results are provided during testing, as no material is taken off site for crushing, cooking, moisture conditioning or other manipulation. The nature and use of a load sensor allows tested material pressure readings to be read in real time and to be electronically transmitted to engineers working off-site, thus saving travel time of skilled workers.

If test results fall outside of limits of variation, additional tests may be set up by merely rotating the position of the penetration head. Device results and device calibrations may use independent tests, such as core samples taken from the testing void.

Multiple load reading versus deformation readings may be found and used to derive modulus results. Errors produced by friction are eliminated. Friction values are not relevant in the disclosed methods and apparatuses.

A minimal amount of operator training is necessary as the operator does not physically manipulate machinery during testing and the operator is never required to drill into material or to crush a sample. An operator is not exposed to hazards such as airborne debris as all pressured material contact occurs within the depths of a void.

The method of forcing a load head or penetration head into the side of a bore hole or cylinder void accurately measures the in place strength of the tested material.

In various embodiments, a convenient configuration of three penetration head configuration accurately measures three useful ranges of strength in the ranges of 1000 to 3000 psi, 3000 to 5000 psi and 5000 psi and above.

The disclosed penetration head configurations reproduce established profiles for the hardness testing of materials; a flat surface for lower strength concrete, a tapered wedge shape for intermediate ranges and a conical shape penetration head for the hardest of concrete.

The invention meets with modern green initiative protocols as little or no noise or waste is produced.

REFERENCE NUMERALS IN THE DRAWINGS

Figure 1:
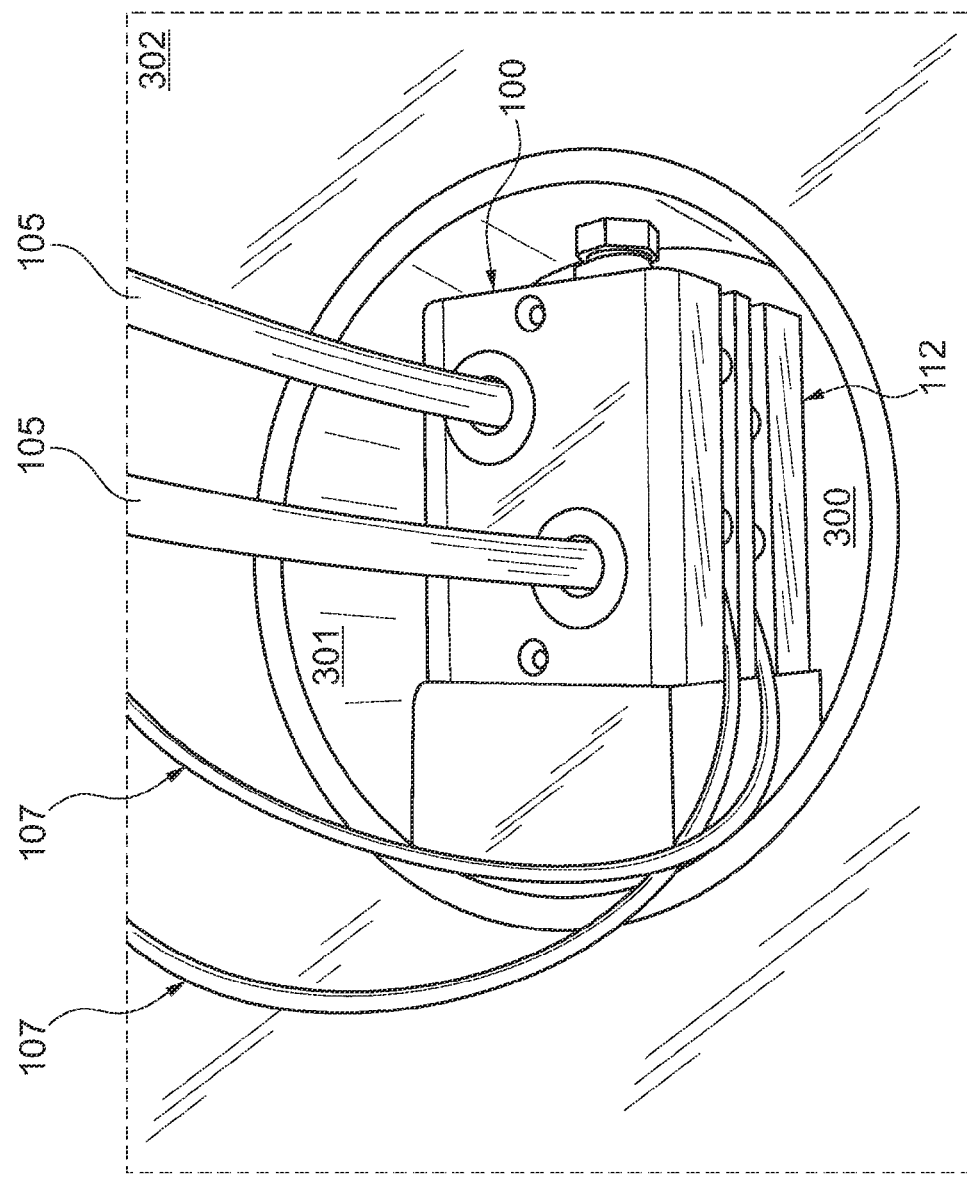
FIG. 1 is an isometric view of one embodiment of the invention.

100 an embodiment of the invention in general, sometimes referred to as "Tavcon."
101 hydraulic ram, having position sensors
102 load centering means or load pivot
103 load cell
104 reaction pad shim
105 hydraulic tube
106 port to accept hydraulic tube
107 electrical wire sometimes attached to position sensors sometimes found within the hydraulic ram 108 curved void within hydraulic ram
109 curved void within rotational block
110 rotational block
111 piston rod, used to urge load head 200
200 penetration head or load head
201 penetration head shown penetrating tested material
300 core hole or core void
301 inner wall of bore hole
302 outer surface of tested material These and other aspects of the present invention will become apparent upon reading the following detailed description in conjunction with the associated drawings.

DETAILED DESCRIPTION OF EMBODIMENTS OF THE INVENTION

The following detailed description is directed to certain specific embodiments of the invention. However, the invention can be embodied in a multitude of different ways as defined and covered by the claims and their equivalents. In this description, reference is made to the drawings wherein like parts are designated with like numerals throughout.

Unless otherwise noted in this specification or in the claims, all of the terms used in the specification and the claims will have the meanings normally ascribed to these terms by workers in the art.

Unless the context clearly requires otherwise, throughout the description and the claims, the words "comprise," "comprising" and the like are to be construed in an inclusive sense as opposed to an exclusive or exhaustive sense; that is to say, in a sense of "including, but not limited to." Words using the singular or plural number also include the plural or singular number, respectively. Additionally, the words "herein," "above," "below," and words of similar import, when used in this application, shall refer to this application as a whole and not to any particular portions of this application.

The above detailed description of embodiments of the invention is not intended to be exhaustive or to limit the invention to the precise form disclosed above. While specific embodiments of, and examples for, the invention are described above for illustrative purposes, various equivalent modifications are possible within the scope of the invention, as those skilled in the relevant art will recognize. For example, while steps are presented in a given order, alternative embodiments may perform routines having steps in a different order. The teachings of the invention provided herein can be applied to other systems, not only the systems described herein. The various embodiments described herein can be combined to provide further embodiments. These and other changes can be made to the invention in light of the detailed description.

All the above references and U.S. patents and applications are incorporated herein by reference. Aspects of the invention can be modified, if necessary, to employ the systems, functions and concepts of the various patents and applications described above to provide yet further embodiments of the invention.

Referring to FIG. 1 a perspective view of one contemplated embodiment is illustrated. One embodiment of the invention, in general 100 is sometimes called the "apparatus", "Tavacon", "unit" "Fietz Material Hardness Tester" or "Fietz Tester". FIG. 1 shows one embodiment with two hydraulic tubes 105 entering a hydraulic ram. Electrical wires are shown to exit the apparatus and the electrical wires 107 are used to transmit information from position sensors found upon the hydraulic ram. For purposes of illustration, the apparatus has been placed within a core hole 300 which is defined by a circular inner wall 301.

Core holes or testing voids may often be found within concrete structures that have been previously tested through the drilling and extraction of core samples. In the related art, core samples may take the shape of a cylinder and leave a cylinder void within the tested material. The removed core samples are usually taken back to a laboratory for testing with the test results reporting the composition of the core sample as a whole. A disadvantage of the prior art is that cylinder core samples may include anomalies of the tested material and thus skew test results. The prior art lacks pin point precision and means to test multiple locations within a core hole.

As shown in FIG. 1 the disclosed apparatus may be placed at any depth within a core hole such that areas of obvious anomaly may be targeted or avoided. Moreover, the apparatus may be rotated to any angular position within a void, and thus even more test locations may be selected. Electrical wires 107 lead to a read out unit, not shown, that displays measurements of ram head travel equal to penetration depth into the tested material and time of travel. This relationship may be plotted or otherwise used to derive material hardness. Other readouts are possible. For purposes of clarity, wires are not always shown in attachment to the load cell. Embodiments of the invention contemplate the use of batteries to power the load cell and the option of using wireless transmitters to transmit information from the load cell to various read out instruments and recorders. For purposes of clarity, wires are not always shown in attachment to the motion sensors found within the hydraulic ram. The motion sensors may be powered via batteries and embodiments of the invention contemplate the use of wireless transmitters to transmit information from the motion sensors to various instruments and recorders.

Figure 2:
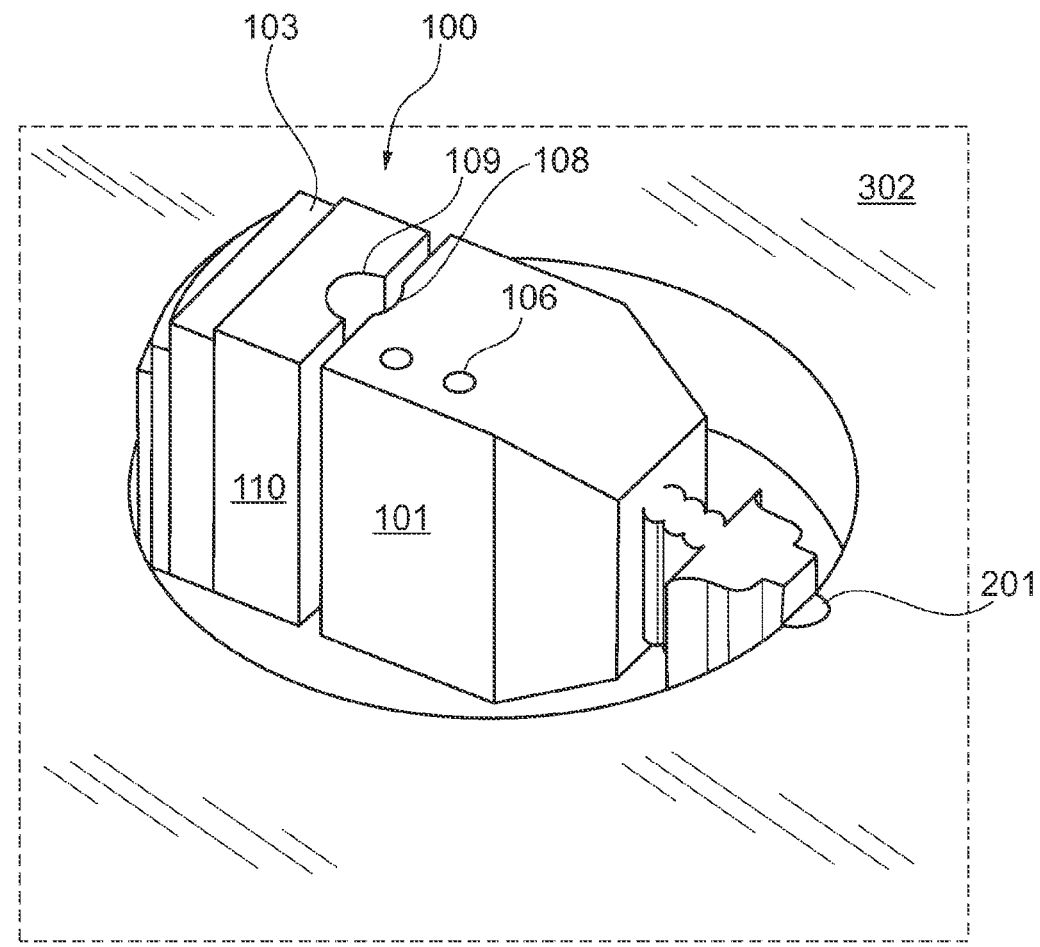
FIG. 2 is an isometric view of one embodiment of the invention.

FIG. 2 shows an alternative embodiment illustrated within a block of concrete, to simulate placement within a core hole. A hydraulic ram 101 is shown as cube type object having ports 106 to accept hydraulic tubes. One side of the hydraulic ram is shown in attachment to a load head 200 with the tip 201 of the load head is shown in state of penetration within the tested material. Alternative embodiments are contemplated wherein various configurations of load heads attach directly to a piston rod 111, such that a separate tip 201 is not needed.

The opposite side of the hydraulic ram defines a curved void 108 similar to the curved void 109 of the adjacent rotational block 110. The optional rotational block 110 may pivot in relationship to the hydraulic ram so as to fit the apparatus within void walls or core walls lacking symmetry. Attached to the rotational block is a load cell 103, with the load cell having means of measuring force required to penetrate the tested material.

Figure 3:
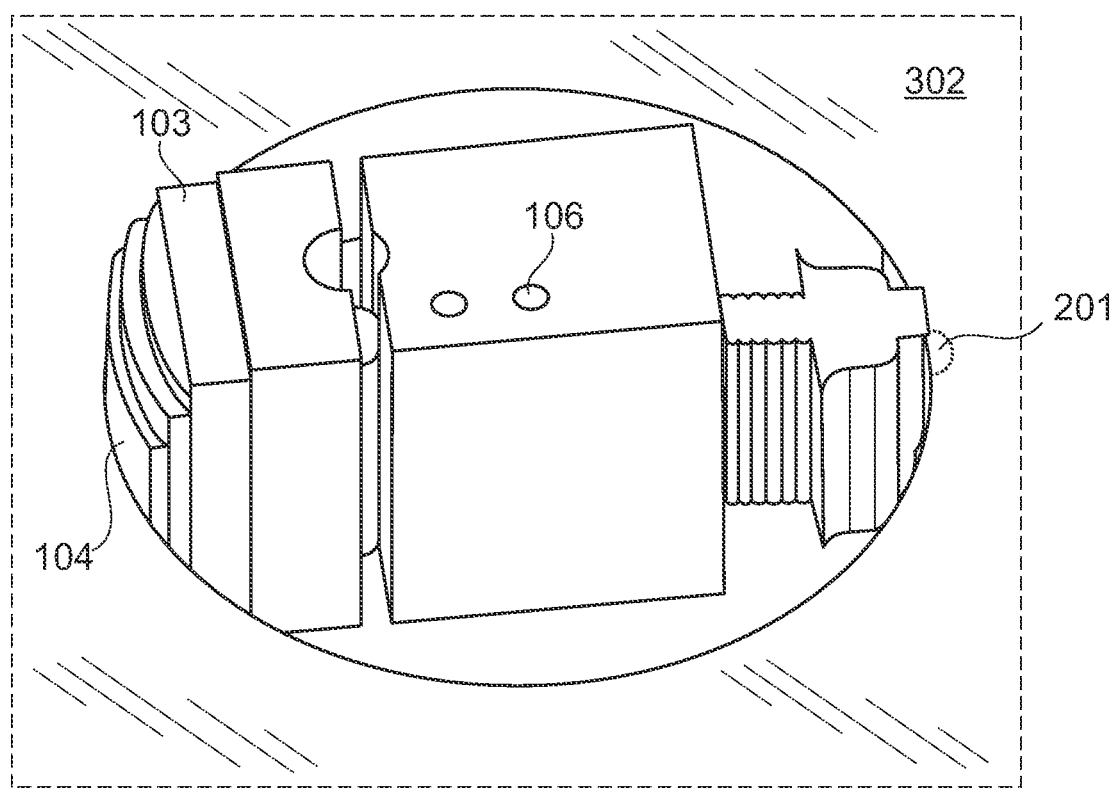
FIG. 3 is an isometric view of one embodiment of the invention.

FIG. 3 presents a perspective view of one contemplated apparatus having one or more reaction pad shims 104 in connection with a load cell 103. The one or more reaction pad shims 104 provide supportive attachment to the load cell and the reaction pad shims comport to the inner wall of a core hole. In some embodiments, reaction pad shims may be added to provisionally support an apparatus within a core hole, as dangling the apparatus by the hydraulic tubes or electrical wires may not be a best practice.

Figure 4:
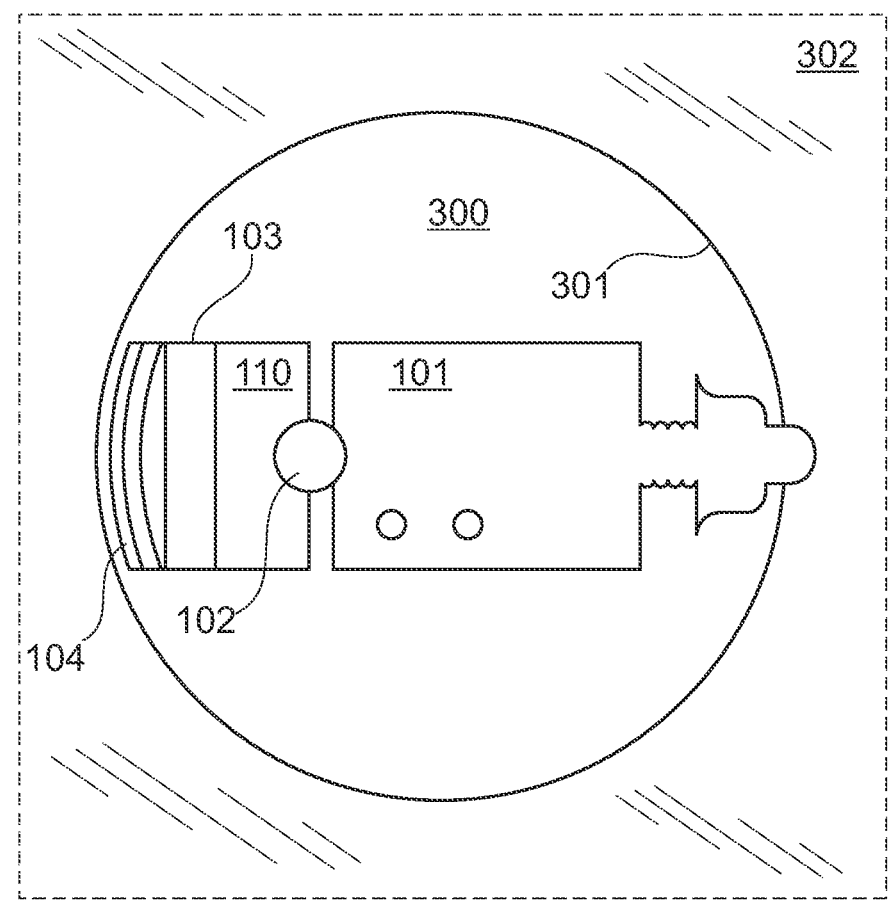
FIG. 4 is a plan view of one embodiment of the invention.

FIG. 4 presents a sectional view of a contemplated apparatus with a load head 200 not in contact with an inner wall 301 of a core hole 300. The sectional view of FIG. 4 presents a clear representation of a load pivot 102 shown to be between and pivotally connected to a rotational block 110 and a hydraulic ram 101. The hydraulic ram 101 is shown with a piston rod 111, with the piston rod having means to move a load head 200 toward an inner wall 301 of a core hole 300. For purposes of discussion and illustration, a load head is sometimes presumed to include a tip 201.

Figure 5:
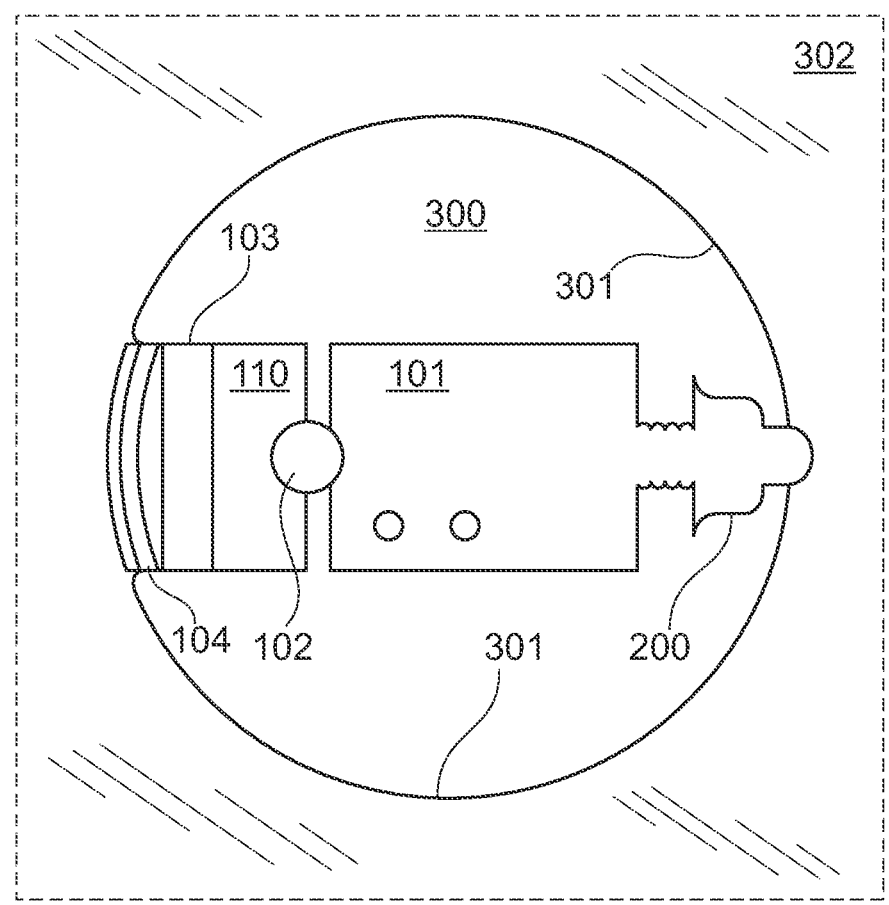
FIG. 5 is a plan view of one embodiment of the invention.

FIG. 5 presents a sectional view of a contemplated apparatus with a load head 200 and reaction pad shim 104, both being in a state of contact with an inner wall 301 of a core hole 300. For purposes of illustration, the piston rod 111 is shown to be more extended as compared to FIG. 4. Other representations and embodiments of the piston rod are contemplated. FIG. 5 shows a tip 201 of a load head to be in a state of penetration within an inner wall 301.

These and other changes can be made to the invention in light of the above detailed description. In general, the terms used in the following claims, should not be construed to limit the invention to the specific embodiments disclosed in the specification, unless the above detailed description explicitly defines such terms. Accordingly, the actual scope of the invention encompasses the disclosed embodiments and all equivalent ways of practicing or implementing the invention under the claims.

While certain aspects of the invention are presented below in certain claim forms, the inventors contemplate the various aspects of the invention in any number of claim forms.

What is claimed is:

1. An apparatus for measuring the hardness of material defining a core hole, the apparatus comprising:
    a) a load head having a first side with a cylindrical tip section and a second side attached to a piston rod with the piston rod being internal to a hydraulic ram with the hydraulic ram moving the piston rod by use of fluid and the hydraulic ram having ports with the ports having means to attach to one or more hydraulic tubes; and
    b) the hydraulic ram defining a curved void;
    c) a rotational block with a first side defining a curved void;
    d) a load pivot disposed within the curved void of the rotational block and the curved void of the hydraulic ram;
    e) the rotational block having a second side attached to a load cell; and
    f) the load cell connected to one or more reaction pad shims.

2. The apparatus of claim 1 wherein the load cell further comprises a calibrated precision hydraulic pressure gage to measure force exerted by the hydraulic ram.

3. The apparatus of claim 1 further comprising an electromechanical driven loading head, with the electromechanical driven loading head incorporating a load cell.

4. The apparatus of claim 1 wherein the hydraulic ram includes one or more position sensors.

5. A method, using the apparatus of claim 1, to measure the hardness of material found within a core hole, the method comprising the steps of:
    a) placing the apparatus of claim 1 into a core hole, the core hole being defined by an inner circular wall;
    b) adding fluid into the hydraulic ram forcing fluid into the load head and a reaction pad shim into opposite sides of the inner circular wall of the core hole; and
    c) measuring the distance traveled by the load head, over time to derive the hardness of the material comprising the inner circular wall.

6. A kit for measuring the hardness of material defining a core void, the kit comprising:
    a) a load head, the load head having a first side and a second side;
    b) the first side of the load head comprising a cylindrical tip section;
    c) a hydraulic ram comprising a piston rod and ports having means to accept hydraulic fluid;
    d) the hydraulic ram defining a curved void;
    e) a load pivot;
    f) a rotational block having a first side defining a curved void;
    g) a load cell; and
    h) one or more reaction pad shims; wherein the curved void of the hydraulic ram and the curved void of the rotational block are configured to have the load pivot disposed within the curved voids.

7. The kit of claim 6 wherein the hydraulic ram comprises position sensors.

8. The kit of claim 6 wherein the load cell further comprises a calibrated precision hydraulic pressure gage.

9. The kit of claim 6 further comprising an electromechanical driven loading head.

* * * * *